(12) United States Patent  
Mittelstadt

(10) Patent No.: US 9,776,023 B2  
(45) Date of Patent: Oct. 3, 2017

(54) RESPIRATORY MASK HAVING A NOSE SUPPORT EXTENSION

(71) Applicant: 3M INNOVATIVE PROPERTIES COMPANY, St. Paul, MN (US)

(72) Inventor: William A. Mittelstadt, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 462 days.

(21) Appl. No.: 14/034,927

(22) Filed: Sep. 24, 2013

(65) Prior Publication Data

US 2015/0083137 A1    Mar. 26, 2015

(51) Int. Cl.
| | |
|---|---|
| *A62B 18/02* | (2006.01) |
| *A62B 18/08* | (2006.01) |
| *A61M 16/06* | (2006.01) |
| *A41D 13/11* | (2006.01) |

(52) U.S. Cl.
CPC .......... *A62B 18/08* (2013.01); *A41D 13/1146* (2013.01); *A61M 16/0605* (2014.02); *A61M 16/0616* (2014.02); *A62B 18/025* (2013.01); *A61M 16/0683* (2013.01)

(58) Field of Classification Search
CPC ........... A62B 7/00; A62B 18/00; A62B 18/08; A62B 18/082; A62B 23/025; A61M 2016/0661; A61M 16/0087–16/0093
See application file for complete search history.

(56) References Cited

U.S. PATENT DOCUMENTS

| | | | | |
|---|---|---|---|---|
| 2,019,928 | A | * | 11/1935 | Punton .................... A62B 23/02 128/201.19 |
| 2,290,885 | A | * | 7/1942 | Lehmberg .......... A41D 13/1146 128/206.15 |
| 2,505,173 | A | * | 4/1950 | Conley ................... A62B 18/00 128/206.15 |
| 2,939,458 | A | | 6/1960 | Lundquist |
| 4,167,185 | A | * | 9/1979 | Lewis ................ A61M 16/0616 128/206.24 |
| 4,739,755 | A | | 4/1988 | White |
| 4,832,017 | A | | 5/1989 | Schnoor |
| 5,062,421 | A | * | 11/1991 | Burns ................... A62B 18/025 128/205.27 |
| 5,143,061 | A | | 9/1992 | Kaimer |
| 5,349,949 | A | | 9/1994 | Schegerin |

(Continued)

FOREIGN PATENT DOCUMENTS

| | | |
|---|---|---|
| DE | 102009057234 | 6/2011 |
| GB | 837250 | 6/1960 |

(Continued)

OTHER PUBLICATIONS

International Application PCT/US2014/055334 Search Report dated Dec. 9, 2014.
European Application 17154233 Search Report dated May 16, 2017.

*Primary Examiner* — Valerie L Woodward

(57) ABSTRACT

A respiratory mask body having a nose region including a seal and a support extension is provided. In an exemplary embodiment, the mask body has a nose region including a support extension which extends in a direction away from the seal and is configured to contact a user's nose at a position beyond the seal.

18 Claims, 5 Drawing Sheets

(56) References Cited

U.S. PATENT DOCUMENTS

| | | | |
|---|---|---|---|
| 5,419,318 A * | 5/1995 | Tayebi | A41D 13/1146 128/205.27 |
| 6,112,746 A | 9/2000 | Kwok | |
| 6,272,693 B1 | 8/2001 | Godoy | |
| 6,581,602 B2 | 6/2003 | Kwok | |
| 7,077,140 B1 | 7/2006 | Berke | |
| 7,082,947 B2 | 8/2006 | Smaldone | |
| 7,287,528 B2 | 10/2007 | Ho | |
| 7,406,965 B2 | 8/2008 | Kwok | |
| 7,610,916 B2 | 11/2009 | Kwok | |
| 7,703,457 B2 | 4/2010 | Barnett | |
| 7,841,988 B2 | 11/2010 | Yamamori | |
| 7,950,392 B2 | 5/2011 | Kwok | |
| 7,975,694 B2 | 7/2011 | Ho | |
| 8,136,523 B2 * | 3/2012 | Rudolph | A61M 16/06 128/206.24 |
| 8,186,348 B2 | 5/2012 | Kwok | |
| 8,230,861 B2 | 7/2012 | Ho | |
| 8,240,302 B1 * | 8/2012 | Tayebi | A62B 18/08 128/201.15 |
| 8,267,089 B2 | 9/2012 | Ho | |
| 8,297,283 B2 | 10/2012 | Hitchcock | |
| 2002/0020416 A1 * | 2/2002 | Namey | A61M 16/06 128/205.25 |
| 2002/0100479 A1 * | 8/2002 | Scarberry | A61M 16/06 128/206.24 |
| 2004/0211426 A1 * | 10/2004 | Lai | A41D 13/1184 128/206.21 |
| 2004/0226563 A1 | 11/2004 | Xu | |
| 2005/0139217 A1 * | 6/2005 | Chiam | A41D 13/11 128/206.19 |
| 2006/0005838 A1 | 1/2006 | Magidson | |
| 2007/0095350 A1 | 5/2007 | Darkin | |
| 2008/0178886 A1 | 7/2008 | Lieberman | |
| 2008/0257354 A1 | 10/2008 | Davidson | |
| 2010/0294281 A1 | 11/2010 | Ho | |
| 2011/0155139 A1 | 6/2011 | Ho | |
| 2011/0174310 A1 | 7/2011 | Burz | |
| 2011/0247628 A1 | 10/2011 | Ho | |
| 2011/0265796 A1 | 11/2011 | Amarasinghe | |
| 2012/0090618 A1 | 4/2012 | Kwok | |
| 2012/0199130 A1 | 8/2012 | Euvrard | |
| 2012/0222681 A1 | 9/2012 | Kwok | |
| 2012/0318272 A1 | 12/2012 | Ho | |

FOREIGN PATENT DOCUMENTS

| | | |
|---|---|---|
| GB | 2275614 | 9/1994 |
| GB | 2412594 | 10/2006 |

* cited by examiner

RESPIRATORY MASK HAVING A NOSE SUPPORT EXTENSION

TECHNICAL FIELD

This disclosure relates to a respiratory protection device, in particular a mask body of a respiratory protection device having a nose region including a seal and a support extension.

BACKGROUND

Respiratory protection devices commonly include a mask body and one or more filter cartridges that are attached to the mask body. The mask body is worn on a person's face, over the nose and mouth, and may include portions that cover the head, neck, or other body parts in some cases. Clean air is made available to a wearer after passing through filter media disposed in the filter cartridge.

Various techniques have been used to support the respiratory protection device on the face of the user while providing an adequate seal to prevent ingress of unwanted debris or contaminants between the mask and face of a user. Many prior mask bodies include a compliant member having a rolled edge that contacts a face of a user to provide both a seal and support for the mask body, while the mask body is maintained on a user with one or more straps of a harness assembly.

SUMMARY

The present disclosure provides for a respiratory mask including a mask body defining a breathable zone of air for a user comprising a nose region, a chin region, and first and second cheek regions, a seal configured to contact the face of a user, the seal defining an opening configured to receive a nose and mouth of a user, and a support extension in the nose region. The support extension extends in a direction away from the seal, and is configured to contact a user's nose at a position beyond the seal. In various exemplary embodiments, the inwardly rolled edge defines an outer peripheral edge of the mask body in the chin region and at least a portion of the first and second cheek regions, and the support extension defines an outer peripheral edge of the mask body in the nose region.

The present disclosure further provides a respiratory mask including a mask body defining a breathable zone of air for a user comprising a nose region, a chin region, and first and second cheek regions, a seal comprising an inwardly rolled edge configured to contact the face of a user and defining an opening configured to receive a nose and mouth of a user, the inwardly rolled edge defining an outer peripheral edge of the mask body in the chin region and at least a portion of the first and second cheek regions, and a support extension in the nose region. The support extension extends in a direction away from the seal and towards the face of a user and contacts a user's nose at a position between the seal and an outer peripheral edge of the mask body. In at least one exemplary embodiment, the support extension does not comprise a rolled edge.

The above summary is not intended to describe each disclosed embodiment or every implementation. The Figures and the Detailed Description, which follow, more particularly exemplify illustrative embodiments.

BRIEF DESCRIPTION OF DRAWINGS

The disclosure may be further explained with reference to the appended Figures, wherein like structure is referred to by like numerals throughout the several views, and wherein.

While the above-identified figures set forth various embodiments of the disclosed subject matter, other embodiments are also contemplated. In all cases, this disclosure presents the disclosed subject matter by way of representation and not limitation. It should be understood that numerous other modifications and embodiments can be devised by those skilled in the art which fall within the scope and spirit of the principles of this disclosure.

DETAILED DESCRIPTION

The present disclosure provides a respiratory protection device having a mask body that includes a nose region having a seal and a support extension. The seal is configured to contact the face of a user to prevent entry of unwanted contaminants or debris, and the support extension extends in a direction away from the seal and contacts a user's nose to provide additional support for the respiratory protection device. The combination of a seal and a support extension in a nose region results in a respiratory mask that provides desired sealing and comfort while reducing unnecessary thickness and bulk that could interfere with eyewear or other personal protective equipment.

Figure 1:
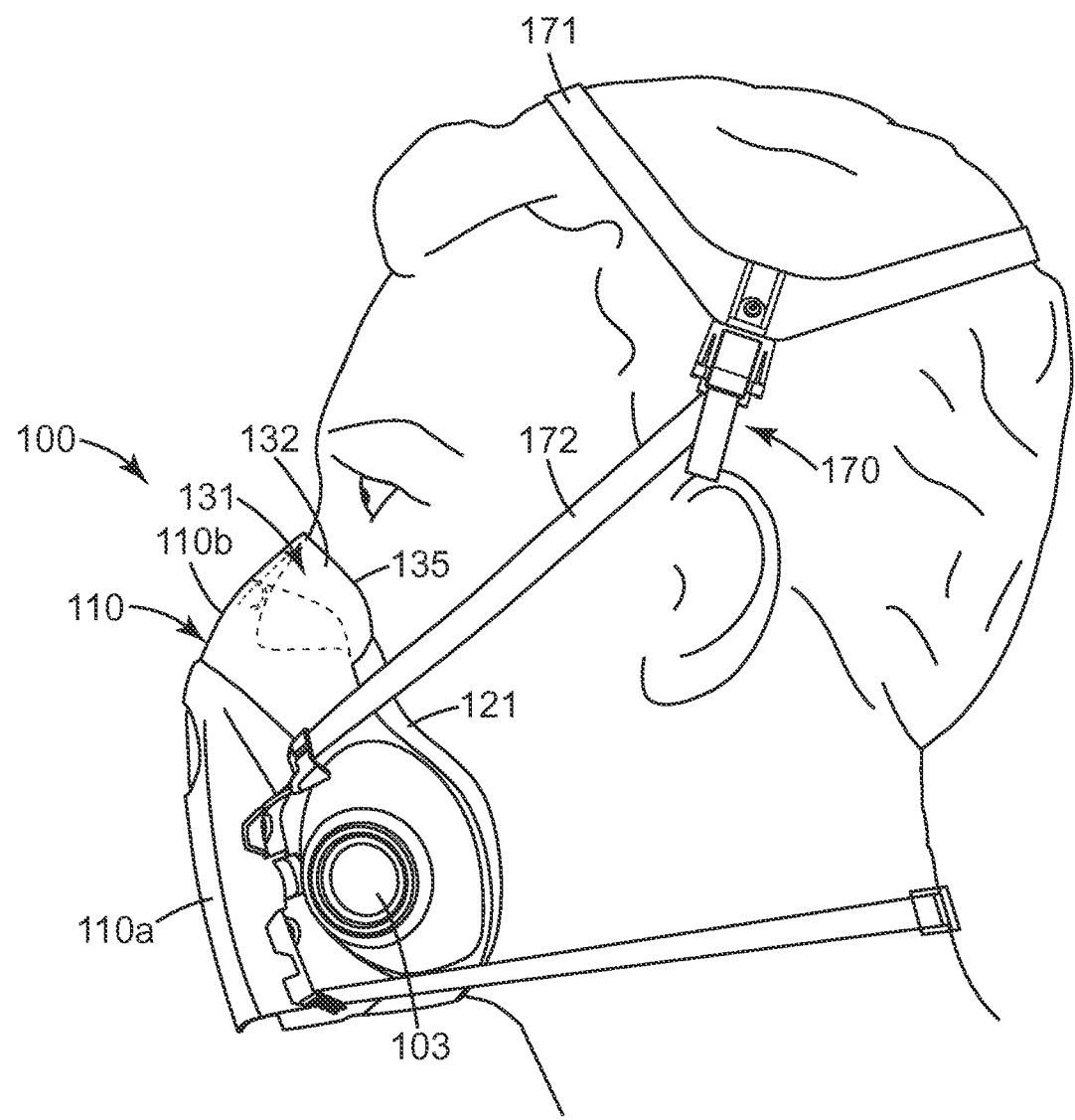
FIG. 1 is a side view of an exemplary respiratory protection system according to the present disclosure positioned on a user.
Figure 2:
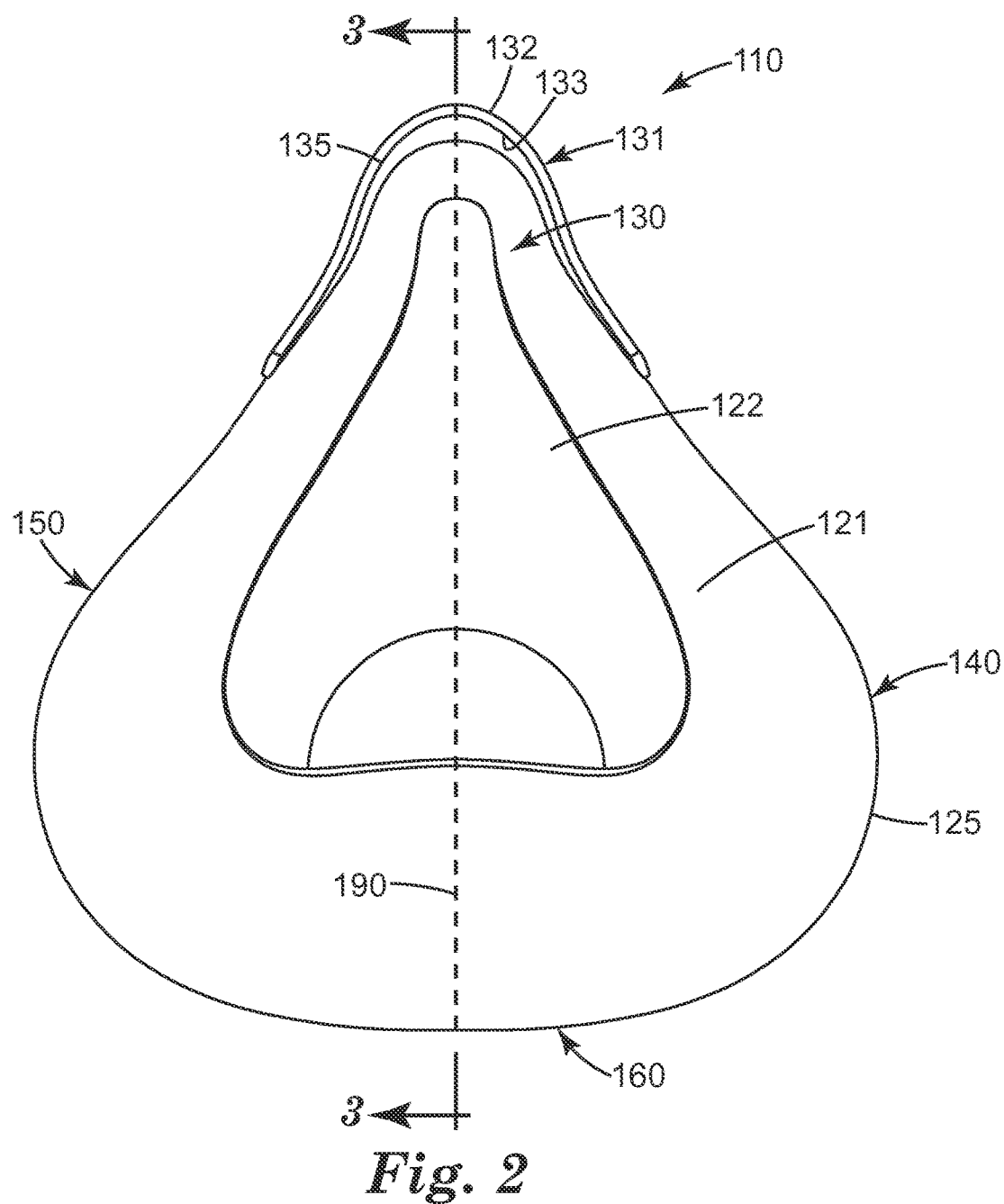
FIG. 2 is a rear view of an exemplary embodiment of a respiratory protection device according to the present disclosure.
Figure 3:
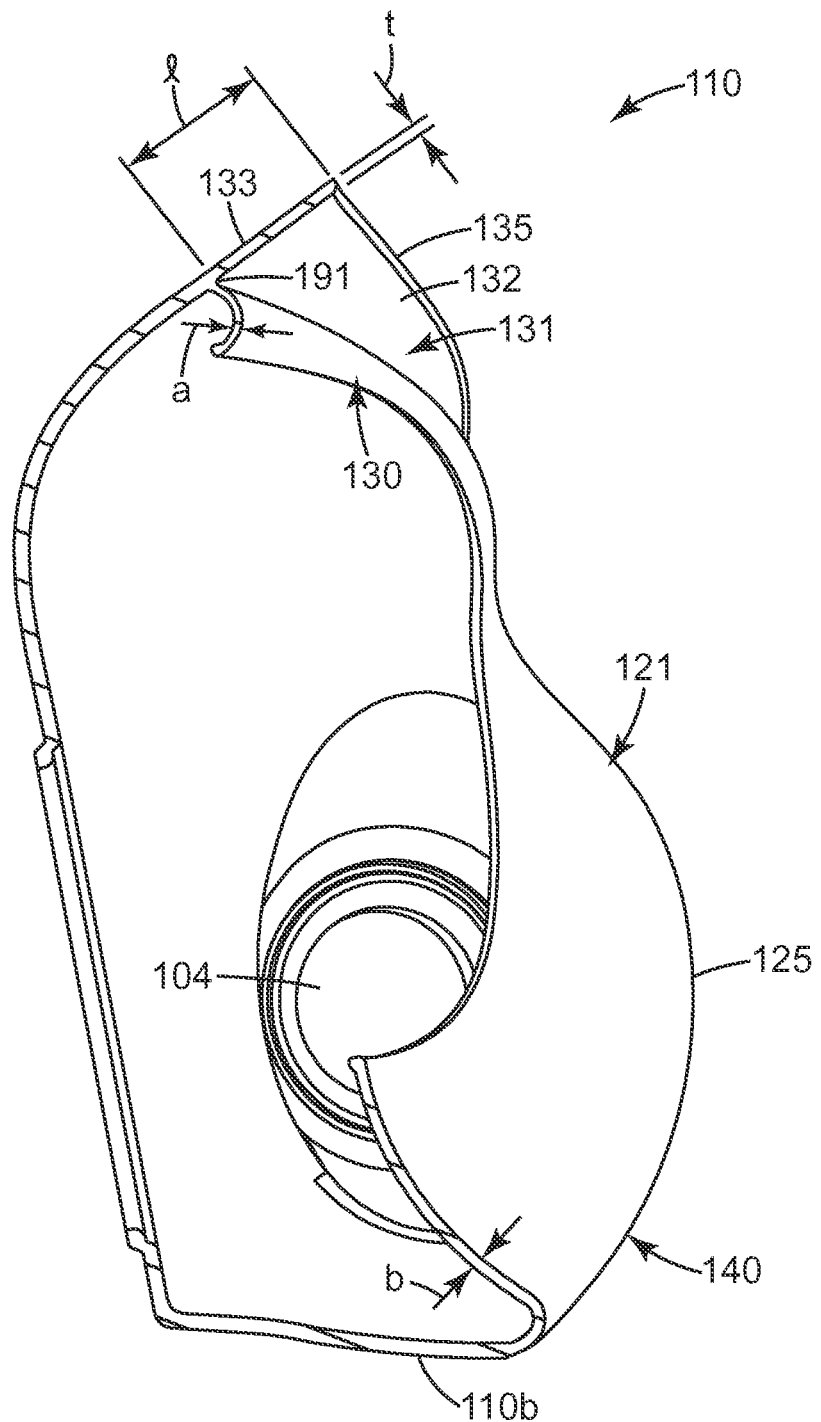
FIG. 3 is a cross-sectional view of an exemplary respiratory protection device according to the present disclosure.

FIGS. 1, 2 and 3 illustrate an exemplary embodiment of a respiratory protection device 100 that may cover the nose and mouth and be used to provide breathable air to a wearer. The respiratory protection device 100 includes a mask body 110 that defines a breathable zone of air for a user and may include a nose region 130, first and second cheek regions, 140, 150, on opposing sides of mask body 110, respectively, and chin region 160. Mask body 110 may include one or more inlet ports, such as inlet ports 103 and 104. One or more breathing air source components, such as filter cartridges (not shown), may be positioned on opposing sides of mask body 110 at first and second inlet ports 103 and 104. The filter cartridges filter air received from the external environment before the air passes into an interior space within the mask body for delivery to a wearer.

In some exemplary embodiments, mask body 110 may include a rigid or semi-rigid portion 110a and a compliant face contacting portion 110b. The face contacting portion of the mask body is compliantly fashioned for allowing the mask body to be comfortably supported over a person's nose and mouth and/or for providing an adequate seal with the face of a wearer. The rigid or semi-rigid portion 110a provides structural integrity to mask body 110 so that it can properly support breathing air source components, such as filter cartridges, for example. In various exemplary embodiments, mask body portions 110a and 110b may be provided integrally or as separately formed portions that are subsequently joined together in permanent or removable fashion.

An exhalation port allows air to be purged from an interior space within the mask body during exhalation by a wearer. In an exemplary embodiment, the exhalation port is located centrally on mask body 110. An exhalation valve is fitted at the exhalation port to allow air to exit due to positive pressure created within mask body 110 upon exhalation, but prevent ingress of external air.

A harness or other support 170 may be provided to support the mask in position about the nose and mouth of a wearer. In an exemplary embodiment, harness 170 includes one or more straps 172 that pass behind a wearer's head. In some embodiments, straps may be attached to a crown member 171 supported on a wearer's head, a suspension for a hard hat, or another head covering.

Respiratory protection device 100 includes a seal 121 configured to contact the face of a user to prevent unwanted contaminants or debris from entering a zone of breathable air within mask body 110. In an exemplary embodiment, seal 121 defines an opening 122 configured to receive or fit over the nose and mouth of a user when mask body 110 is positioned for use. Exemplary seal 121 thus surrounds an entirety of mask body 110 to provide sealing contact with the face of a user.

In an exemplary embodiment best viewed in FIGS. 2 and 3, seal 121 includes an inwardly rolled edge. A rolled edge provides a snug and comfortable fit over a user's nose and against a user's cheeks and chin while providing a consistent seal against the contours of a user's face. In an exemplary embodiment, the rolled edge is integrally formed with compliant face-contacting portion 110b of mask body 110. The rolled edge readily flexes and conforms to a user's face when positioned for use. In an exemplary embodiment, the rolled edge of seal 121 defines an outer peripheral edge 125 of the mask body in at least a portion of first and second cheek regions 140, 150 and chin region 160.

Referring to FIGS. 1, 2 and 3, nose region 130 of mask body 110 includes a support extension 131 which extends in a direction away from the seal 121 and contacts a user's nose. In an exemplary embodiment, support extension 131 extends beyond the seal and towards the user's face. Support extension 131 defines an outer peripheral edge 135 of nose region 130 and may be configured to contact a user's nose at a position beyond seal 121, for example between seal 121 and outer peripheral edge 135 and/or at outer peripheral edge 135. In an exemplary embodiment, support extension 131 includes an outer surface 132 and an inner surface 133 separated by a thickness (t). When positioned for use, inner surface 133 may contact a user's nose and adjacent facial area to provide additional support and stability for mask body 110. In an exemplary embodiment, seal 121 provides sufficient sealing on the face of a user and inner surface 133 need not provide complete and uniform contact on a user's nose. In at least one exemplary embodiment, support extension 131 does not include a substantial rolled edge.

In some embodiments, support extension 131 may be formed of a single layer of material. A single layer of material reduces interference with eyewear or other personal protective equipment that a user may desire to wear in combination with respiratory protection device 100. Alternatively, support extension 131 may be formed of one or more layers of material joined together, by bonding for example, or other suitable methods as known in the art, such that support extension 131 is not unduly thick so as to cause interference with eyewear.

Compliant face-contacting member 110b and seal 121 may be made of any suitable flexible material that may be comfortably positioned on the face of a user. In various exemplary embodiments, compliant face-contacting member 110b is made of silicone, rubber, or other suitable materials.

The thicknesses of seal 121 and support extension 131 may be configured to provide adequate sealing and support, respectively, while minimizing unnecessary bulk of mask body 110. In an exemplary embodiment in which seal 121 comprises a rolled edge integral to compliant face-contacting portion 110b, a thickness of seal 121 may be substantially uniform and similar to the thickness of the remainder of compliant face-contacting portion 110b. In other exemplary embodiments, a thickness of the rolled edge of seal 121 may differ from a thickness of compliant face-contacting portion 110b, and may vary at different locations of seal 121. In various exemplary embodiments, seal 121 includes a rolled edge having a thickness at any particular location between approximately 0.4 mm and 2.0 mm, 0.55 mm and 1.2 mm, or of about 0.65 mm. Such thicknesses may provide sufficient durability while providing a relatively lightweight mask body 110.

In some exemplary embodiments, the thickness of seal 121 in nose region 130 is generally less than a thickness in first and second cheek regions 140, 150 and/or chin region 160. The presence of seal 121 and support extension 131 in nose region 130 allows seal 121 to be relatively thinner in the nose region because seal 121 does not need to also be a primary source of support for mask body 110. The presence of support extension 131 also allows seal 121 to contact the nose of a user lower and closer to the tip of the nose. A thinner seal positioned closer to the tip of the nose may provide greater comfort for a user, especially during extended periods of use.

Accordingly, the overall thickness of the nose region can be reduced to improve visibility and compatibility with eyewear or other personal protective equipment and to promote proper positioning of mask body 110 on the face of a user. For example, seal 121 has a thickness (a) in nose region 130 between approximately 0.4 mm and 2.0 mm, or 0.55 mm and 1.2 mm, or of approximately 0.65 mm, and a thickness (b) in a chin region between approximately 0.8 mm and 3.0 mm, or 1.0 mm and 2.0 mm, or of approximately 1.5 mm. In various exemplary embodiments, thickness (a) of seal 121 in nose region 130 is between approximately 30% and 90%, 45% and 75%, or approximately 45% of thickness (b) of seal 121 in chin region 160. In an exemplary embodiment, seal 121 having such thickness is compliant to provide a comfortable fit.

Certain features of a respiratory protection device according to the present disclosure may be further understood in view of a reference plane defined with respect to mask body 110 and shown in FIG. 2. With respiratory protection device positioned vertical as when positioned for use, a mid-sagittal plane 190 bisects respiratory protection device 100 into imaginary left and right halves. Support extension 131 has a length (l) along mid-sagittal plane 190 between seal 121 and outer peripheral edge 135. In various exemplary embodiments, a length l between approximately 5 mm and 30 mm, approximately 9 mm and 20 mm, or of approximately 12 mm, results in a support extension that provides stability and support while generally providing comfortable positioning on the nose of a user. In various exemplary embodiments, length (l) may be measured between an intersection 191 of an outer edge of seal 121 and support extension 131, and an outer peripheral edge 135 of nose region 130.

In an exemplary embodiment, support extension 131 has total thickness (t) between an outer surface 132 and an inner surface 133, and substantially uniform at all points along length (l), of between approximately 0.7 mm and 3 mm, 1 mm and 2 mm, or of approximately 1.3 mm. Such a thickness minimizes interference with eyewear or other personal protective equipment that may be worn in combination with respiratory protection device 100. In other exemplary embodiments, thickness (t) of support extension 131 varies along length (l).

A respiratory protection device having a mask body as described herein provides several benefits. While elastomeric face masks of prior respiratory protection devices may interfere with eyewear, such as safety eyewear or prescription eyewear, the present disclosure provides a mask that is more suitable for use with eyewear. A mask body having a nose region that includes a support extension separate from a seal allows the thickness of the seal to be relatively less, and the overall thickness of the mask body in a nose region to be reduced. Rather than requiring a nose region seal to provide primary sealing and support for the mask body as in many prior devices, a support extension may provide significant support. The presence of a support extension also allows a seal in the nose region to be positioned lower and closer to the tip of a user's nose. The presence of a support extension results in sufficient support and stability of the mask body, even with a relatively thinner seal in the nose region. Eyewear may be worn in combination with such a mask body with the eyewear supported on the nose of a user above the support extension and/or supported on the support extension of the mask body.

Figures 4A, 4B:
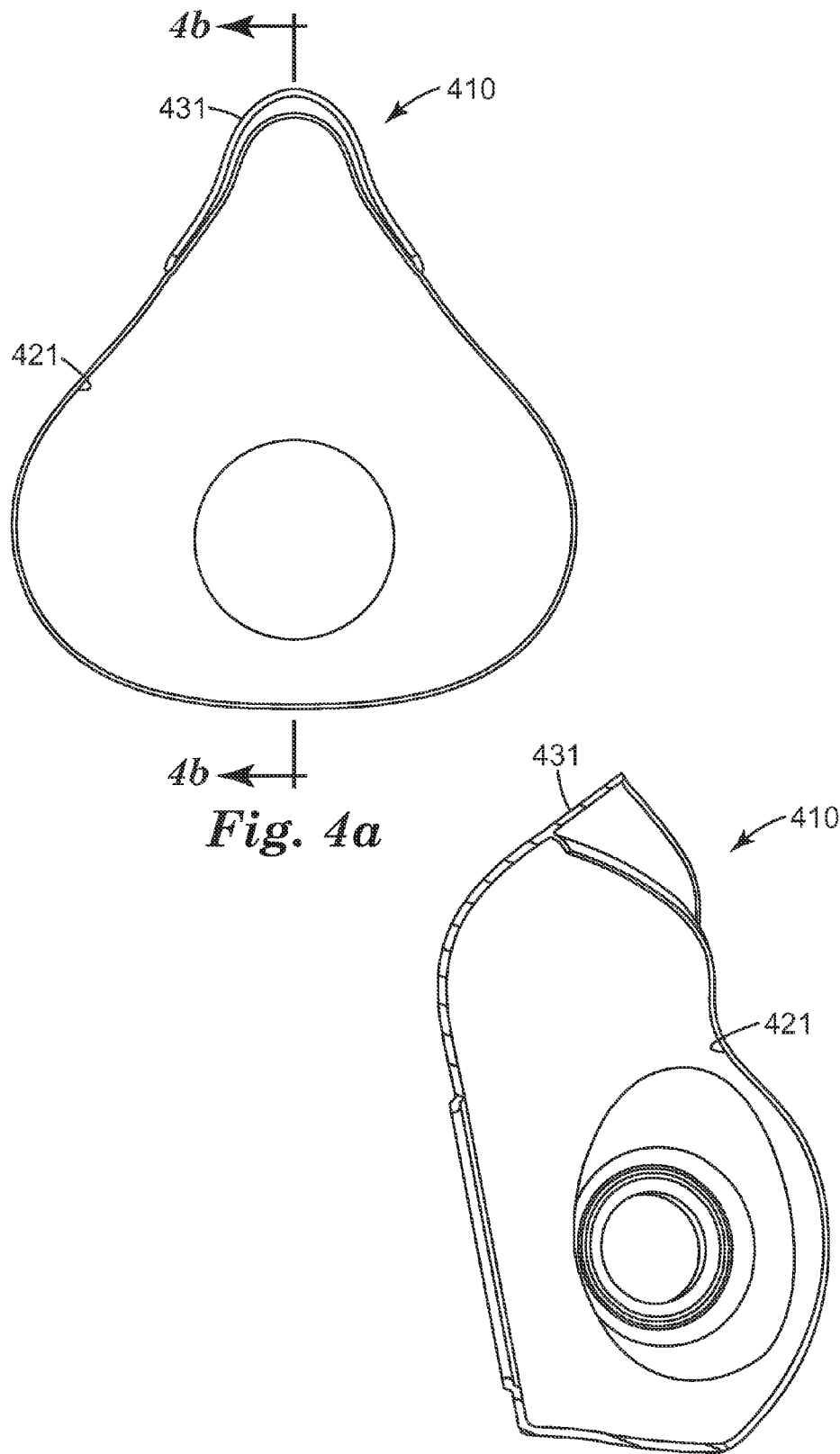
FIG. 4a is a rear view of an exemplary embodiment of a respiratory protection device according to the present disclosure.
FIG. 4b is a cross-sectional view of an exemplary respiratory protection device according to the present disclosure.
Figure 5:
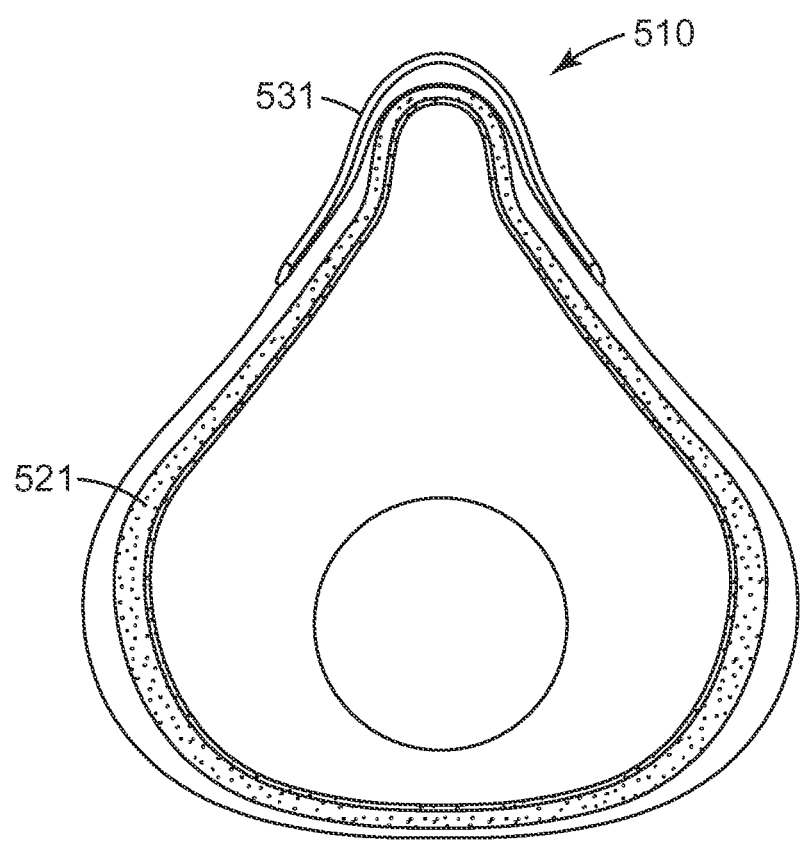
FIG. 5 is a rear view of an exemplary embodiment of a respiratory protection device according to the present disclosure.

In various exemplary embodiments, other sealing features may be provided in combination with or in place of a rolled edge. FIG. 4 shows an exemplary mask body 410 including a seal 421 and support extension 431. Seal 421 may extend generally straight outwardly and/or roll slightly outwardly when mask body 410 is positioned on the face of a user. FIG. 5 shows another exemplary mask body 510 including a seal 521 and support extension 531. Seal 521 includes a foam, gel, or other suitable material positioned on mask body 510 to make sealing contact with a face of a user when mask body 510 is positioned for use. In some exemplary embodiments, the foam is made of a relatively soft and compliant material, and may include polypropylene, styrene-ethylene-butylene-styrene, polyurethane, thermoplastics, thermosets, rubber, and/or other suitable materials. In other exemplary embodiments, the gel or other suitable material may be encapsulated to provide a relatively soft and compliant material that may contact the face of a user and provide an appropriate seal.

The foregoing detailed description and examples have been given for clarity of understanding only. No unnecessary limitations are to be understood there from. It will be apparent to those skilled in the art that many changes can be made in the embodiments described without departing from the scope of the disclosure. Any feature or characteristic described with respect to any of the above embodiments can be incorporated individually or in combination with any other feature or characteristic, and are presented in the above order and combinations for clarity only. Thus, the scope of the present disclosure should not be limited to the exact details and structures described herein, but rather by the structures described by the language of the claims, and the equivalents of those structures.

What is claimed is:

1. A respiratory mask, comprising:
   a mask body defining a breathable zone of air for a user comprising a nose region, a chin region, and first and second cheek regions;
   a seal configured to contact the face of a user, the seal defining an opening configured to receive a nose and mouth of a user; and
   a support extension in the nose region, wherein the support extension is only present at the nose region of the mask body;
   wherein the support extension extends in a direction away from the seal, is configured to contact a user's nose at a position outside the seal, and does not provide complete and uniform contact on a user's nose.

2. The respiratory mask of claim 1, wherein the mask body comprises a rigid portion and a compliant face-contacting portion.

3. The respiratory mask of claim 1, wherein the seal is integrally formed with a compliant face-contacting portion of the mask body.

4. The respiratory mask of claim 1, wherein the seal comprises an inwardly rolled edge.

5. The respiratory mask of claim 4, wherein the inwardly rolled edge defines an outer peripheral edge of the mask body in the chin region and at least a portion of the first and second cheek regions.

6. The respiratory mask of claim 1, wherein the seal comprises a material selected from the group consisting of foam and gel.

7. The respiratory mask of claim 1, wherein the support extension comprises an outer surface and an inner surface separated by a thickness (t).

8. The respiratory mask of claim 7, wherein at least a portion of the inner surface of the support extension is configured to contact the nose of a user when the mask body is positioned for use.

9. The respiratory mask of claim 7, wherein 0.7 mm<t<3 mm.

10. The respiratory mask of claim 1, wherein the support extension comprises a single layer of material.

11. The respiratory mask of claim 1, wherein the support extension does not comprise a rolled edge.

12. The respiratory mask of claim 1, further comprising one or more inlet ports and one or more breathing air source components in fluid communication with the one or more inlet ports.

13. The respiratory mask of claim 1, wherein the support extension defines an outer peripheral edge, wherein the outer peripheral edge of the support extension is configured to contact the user's nose at the position outside the seal.

14. A respiratory mask, comprising:
    a mask body defining a breathable zone of air for a user comprising a nose region, a chin region, and first and second cheek regions;
    a seal configured to contact the face of a user, the seal defining an opening configured to receive a nose and mouth of a user; and
    a support extension in the nose region, wherein the support extension defines an outer peripheral edge of the mask body in the nose region,
    wherein the support extension extends in a direction away from the seal, is configured to contact a user's nose at a position outside the seal, and does not provide complete and uniform contact on a user's nose.

15. The respiratory mask of claim 14, wherein a mid-sagittal plane bisects the mask into imaginary left and right halves, and the support extension has a length (l) along the mid-sagittal plane between the seal and the outer peripheral edge, wherein 5 mm<l<30 mm.

16. A respiratory mask, comprising:
a mask body defining a breathable zone of air for a user comprising a nose region, a chin region, and first and second cheek regions;
a seal comprising an inwardly rolled edge configured to contact the face of a user and defining an opening configured to receive a nose and mouth of a user, the inwardly rolled edge defining an outer peripheral edge of the mask body in the chin region and at least a portion of the first and second cheek regions; and
a support extension in the nose region;
wherein the support extension extends in a direction away from the seal and adapted to be towards a face of a user, wherein the support extension is adapted to contact a user's nose at a position outside the seal between the seal and an outer peripheral edge of the support extension, the support extension not comprising a rolled edge, wherein the support extension does not provide complete and uniform contact on a user's nose.

17. The respiratory mask of claim 16, wherein the support extension comprises a single layer.

18. The respiratory mask of claim 16, wherein a mid-sagittal plane bisects the mask into imaginary left and right halves, and the support extension has a length (l) along the mid-sagittal plane between the seal and the outer peripheral edge of the support extension, wherein 9 mm<l<20 mm.

* * * * *